US00PP28586P3

(12) United States Plant Patent
Olesen

(10) Patent No.: US PP28,586 P3
(45) Date of Patent: Oct. 31, 2017

(54) ***CLEMATIS* PLANT NAMED 'EVIPO050'**

(50) Latin Name: *Clematis viticella*
Varietal Denomination: Evipo050

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 46 days.

(21) Appl. No.: 14/756,246

(22) Filed: Aug. 20, 2015

(65) Prior Publication Data

US 2017/0055415 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Poulsen Roser A/S, Perfection by Poulsen, Jan. 2013.*

* cited by examiner

*Primary Examiner* — Keith Robinson

(57) ABSTRACT

A new *Clematis* plant with a compact growth habit, profuse, light pink flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo050'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2001 and the resulting seeds were planted the following winter in a controlled environment in Guernsey, Channel Islands, United Kingdom. The new variety named 'Evipo050' originated as a single seedling from the stated cross.

The new *clematis* plant may be distinguished from its female seed parent and male pollen parent by the following characteristics. The female seed parent has flowers which are deep pink, while the new plant has flowers which are light pink. The male pollen parent has a growth height less than that of the new cultivar.

The objective of the hybridization of this *clematis* plant was to create a new and distinct variety for nursery culture with unique qualities such as:

1. Uniform and abundant light pink flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo050' was selected by Mogens N. Olesen and Raymond J. Evison in their *clematis* development program in the Channel Islands, United Kingdom in 2002. Asexual reproduction of 'Evipo050' by means of vegetative stem cuttings and traditional layering was first performed by Mogens N. Olesen and Raymond J. Evison in the nursery during the summer of 2002. This initial and subsequent asexual propagations have demonstrated that the characteristics of 'Evipo050' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo050'. Specifically illustrated in the drawing are flowers at various stages of development, flower in parts, a cluster of flower buds on the stem, leaves, and bare stems. Plants shown are 2 years of age.

DETAILED DESCRIPTION OF THE VARIETY

The following is a detailed description of 'Evipo050', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evione' described and illustrated in U.S. Plant Pat. No. 10,222 are compared to 'Evipo050' in Chart 1.

CHART 1

| | 'Evipo050' | 'Evione' |
|---|---|---|
| Flower diameter | 100 mm | 130 to 180 mm |
| Tepal upper surface | Red-Purple Group 60A with intonations of Red-Purple Group 61B | Purple 76A with red/purple central bar 71A |
| Tepal count | 9 | 6, sometimes 8 |

FLOWER AND FLOWER BUD

Blooming habit: Continuous. The natural flowering period is generally from April to September.

Flower bud:

*Size*.—Normally 35 mm in length. Bud diameter is 15 mm.

*Texture*.—Very pubescent.

*Bud form*.—Elliptic.

*Bud color*.—Yellow-Green Group 145C with intonations of Greyed-Red Group 182B towards apex.

Peduncle:

*Surface texture*.—Pubescent.

*Length*.—On average 45 mm.

*Diameter*.—3 mm.

*Color*.—Yellow-Green Group 144B.

*Strength*.—Moderately strong.

Receptacle:

*Surface texture*.—Pubescent.

*Shape*.—Broad funnel.

*Size*.—2 mm (h)×4 mm (w).

*Color*.—Yellow-Green Group 144B.

Flower arrangement:

*Location on vine*.—New and old growth.

*Borne*.—Normally in clusters of 3 flowers.

*Attitude*.—Flowers are typically oriented upwards and outwards on the vine.

Flower bloom:

*Size*.—On average, flowers are 100 mm in diameter and 25 mm in depth.

*Profile*.—Open flowers are flat.

*Fragrance*.—None.

*Lasting quality*.—Flowers normally remain up to 10 days on the plant.

Tepals:

*Tepal color*.—Upon opening, the upper surface is Red-Purple Group 60A with intonations of Red-Purple Group 61B. Upper surface changes to Purple Group 75A with intonations of 75D. Occasionally splotches of White Group 155A. The lower surface is Purple Group 76D with marginal intonations of Red-Purple Group N74D. The lower surface central bar is Orange-White Group 159C. After opening the upper surface is Red-Purple Group 70A with a central bar of Red-Purple Group 63A.

*Quantity*.—Normally 9 tepals.

*Size*.—55 mm in length by 40 mm wide.

*Shape*.—Individual tepal shape is elliptic. The tepal apex is mucronate. The tepal base is obtuse.

*Apex recurvature*.—None.

*Tepal cross section*.—Flat.

*Margins*.—Entire. Slight undulations of margin observed.

*Persistence*.—Tepals drop off cleanly.

*Arrangement*.—Overlapping.

Reproductive organs:

*Arrangement*.—Somewhat compact.

*Pollen*.—None observed.

*Anthers*.—Size: 5 mm in length. Color: Purple Group 79A. Quantity: On average, 35.

*Filaments*.—Color: Yellow Group 1D. Length: About 6 mm.

*Pistils*.—Quantity: On average, 20.

*Styles*.—Color: Green-White Group 157A. Length: 10 mm.

PLANT

Plant form: Climbing.

Plant growth: Moderately vigorous.

Size: Seasons growth attains 50 to 75 cm in height. Average spread is 50 cm.

Stems:

*Color*.—Juvenile stems are Yellow-Green Group 144B. Mature stems are Greyed-Red Group 182A.

*Internodes*.—On average, 8 cm between nodes.

*Length*.—Normally 30 cm from the base of the plant to the flowering portion of the stem.

*Diameter*.—Normally 2 mm.

*Texture*.—Mature stems are ribbed.

Plant foliage:

*Leaf characteristics*.—Deciduous.

*Arrangement*.—Trifoliate.

*Leaf size*.—Compound leaves are normally 140 mm (l)×110 mm (w). Leaflets are normally 42 mm (l)×23 mm (w).

*Abundance*.—On average 1 leaf per 10 cm of stem.

*Leaf color*.—Juvenile upper Yellow-Green Group 144A. Juvenile lower Yellow-Green Group 144B. Mature upper Yellow-Green Group 147B. Marginal intonations of Greyed-Red Group 178B. Mature lower Yellow-Green Group 147C.

*Stipules*.—Absent.

*Petioles*.—Size: Normally 80 mm in length by 1 mm diameter. Texture: Smooth. Color: Greyed-Orange Group 173A above, underneath Yellow-Green Group 144B.

*Petioloule*.—Size: Normally 40 mm in length by 1 mm diameter. Texture: Smooth. Color: Greyed-Orange Group 173A above, underneath Yellow-Green Group 144B.

*Leaflet shape*.—Generally elliptic. The base is rounded to cordate. The apex is acute.

*Margin*.—Entire.

*Surface*.—The upper side is smooth. The lower side is smooth.

*Thickness*.—Average.

*Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo050', substantially as described and illustrated , due to its abundant light pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

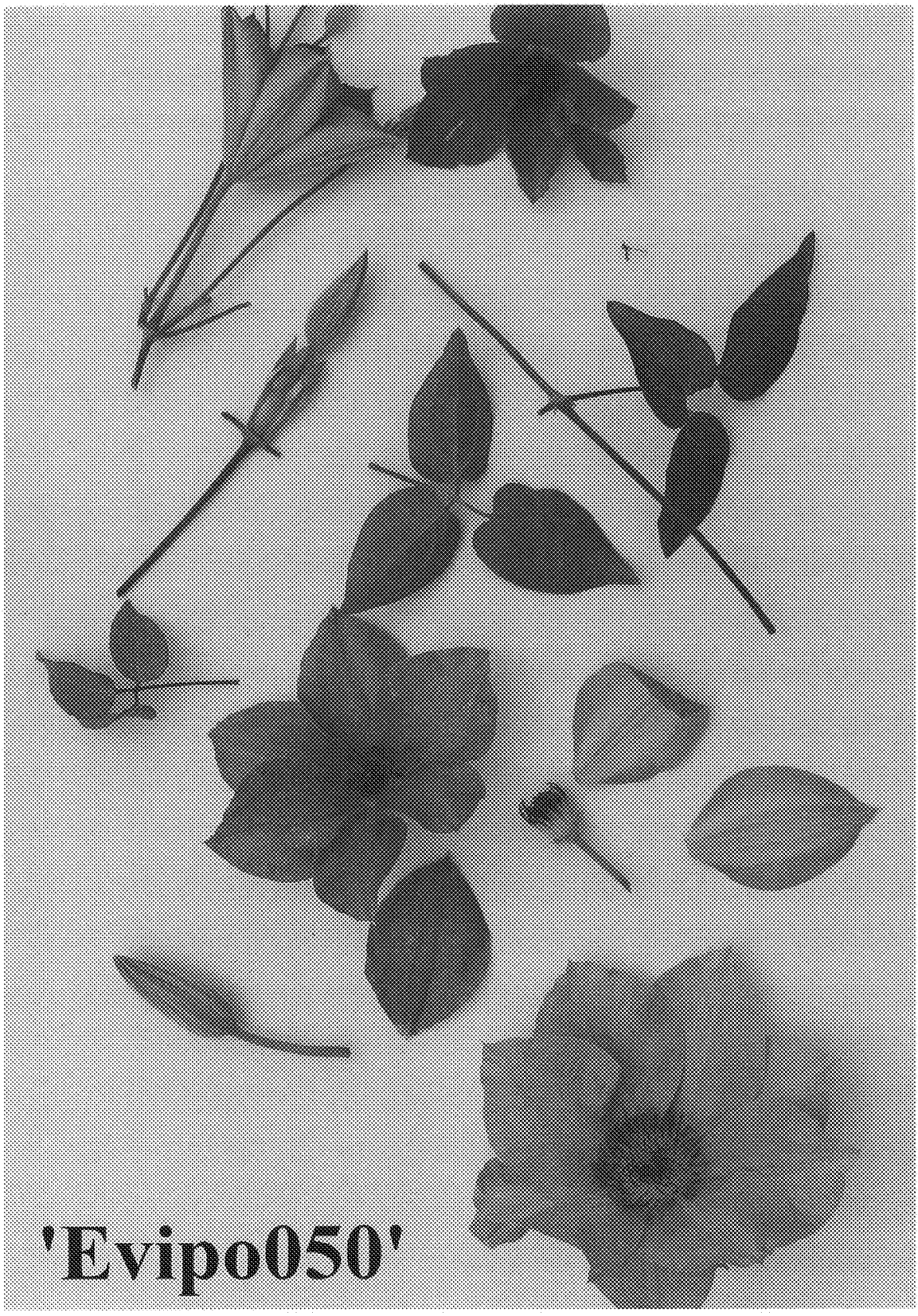
'Evipo050'